United States Patent [19]

Rieke

[11] Patent Number: 4,493,096

[45] Date of Patent: Jan. 8, 1985

[54] METHOD OF X-RAY IMAGING USING SLIT SCANNING WITH CONTROLLED TARGET ERASE

[75] Inventor: Richard J. Rieke, Brookfield, Wis.

[73] Assignee: General Electric Company, Milwaukee, Wis.

[21] Appl. No.: 450,589

[22] Filed: Dec. 17, 1982

[51] Int. Cl.³ .......... A61B 6/00; H04N 7/18

[52] U.S. Cl. .......... 378/99; 358/111; 378/7

[58] Field of Search .......... 378/146, 99, 7; 358/111

[56] References Cited

U.S. PATENT DOCUMENTS

| | | | |
|---|---|---|---|
| 4,220,890 | 9/1980 | Beekman | 313/240 |
| 4,380,818 | 4/1983 | Pfeiler | 378/99 |
| 4,404,591 | 9/1983 | Bonar | 358/111 |

*Primary Examiner*—Alfred E. Smith
*Assistant Examiner*—T. N. Grigsby
*Attorney, Agent, or Firm*—Alexander M. Gerasimow; Douglas E. Stoner

[57] ABSTRACT

A method of x-ray imaging the internal features of an object undergoing examination in which the object is scanned with a beam of x-ray radiation. The radiation is transmitted through the object as primary imaging radiation and as scatter radiation. The image-degrading effect of scatter radiation is reduced by employing a controlled TV camera tube target erase. The controlled target erase consists of a camera tube target raster scan by an electron beam controlled in the vertical position so as to immediately precede in position on the target the latent image charge pattern moduled thereon by exposure to primary imaging radiation. In this manner, the scatter radiation that leads in position the primary radiation is erased from the target prior to read out and, therefore, does not contribute to the TV image formation. The method is also effective in reducing the effects of electron scatter occurring in an image-intensifier tube and optical scatter occurring in system optical elements.

14 Claims, 3 Drawing Figures

METHOD OF X-RAY IMAGING USING SLIT SCANNING WITH CONTROLLED TARGET ERASE

BACKGROUND OF THE INVENTION

This invention relates to a method of x-ray imaging with apparatus having a source of ionizing radiation, and an imaging device for converting the radiation to a wavelength suitable for detection by a television camera. More specifically, this invention relates to a method of x-ray slit scanning with controlled TV camera tube target erase so as to reduce substantially the effects of scatter.

A typical use for such imaging is as a medical diagnostic modality. In such applications, primary imaging radiation, such as x-ray radiation which has been intensity modulated by passage through a patient, strikes the input screen of an image-intensifier tube where it is converted to an electron latent image. Electrodes contained in the tube minify the image and accelerate the electrons toward a luminescent output screen of the image-intensifier tube. An image having increased brightness is produced on the output screen in accordance with the spatial modulation on the x-ray radiation. A television camera and monitor are used to display the image. Frequently, a photographic camera is also used to record images of diagnostic interest.

High image quality, as measured by image resolution, contrast, and x-ray photon noise, is very desirable in such applications of the imaging apparatus. Image quality is, however, degraded by scatter which affects contrast and noise. One type of scatter, which will be referred to as x-ray scatter, is produced by deflection of x-rays from their normal paths by the body undergoing examination. Such x-rays strike the input screen of the image-intensifier tube and induce a spurious response which is detected by the television camera, for example, and displayed on the television monitor. Additional scatter is produced by scattered electrons in the image-intensifier tube and by other system light optical elements, further degrading image quality. Scatter acts to increase the overall brightness of the image background thereby decreasing image contrast. Therefore, it will be appreciated that minimizing the effects of scatter will have the desirable effect of increasing image contrast, reducing noise, and concomitantly improving image quality, since both scatter and primary x-ray radiation contribute to x-ray photon noise.

One known method of reducing the deleterious effects of x-ray scatter is to position a radiation-absorbing grid in front of the input surface of an imaging device, such as an image-intensifier tube, a fluoroscopic phosphor screen, or a photographic camera. An example of an imaging apparatus using a grid is disclosed in U.S. Pat. No. 4,220,890. Undesirable effects associated with the use of such a grid include the attenuation of non-scattered primary imaging radiation producing grid shadow lines which can obscure image detail behind the shadow. Attenuation of the primary imaging radiation also has the effect of decreasing the signal-to-noise ratio of the image. Additionally, radiation-absorbing grids do not reduce scatter originating in the image-intensifier tube and in system optical elements.

Another method of scatter reduction is described by G. T. Barnes and I. A. Brezovich, "The Design and Performance of a Scanning Multiple Slit Assembly," *Medical Physics,* Vol. 6, No. 3 (May/June 1979), pp. 197–204. In this method, a series of narrow slits for collimating the x-ray beam is positioned between the x-ray source and the patient. A second series of scatter-eliminating slits is disposed between the patient and the x-ray conversion device (e.g., an x-ray image-intensifier tube) and are aligned with the x-ray collimating slits. During an exposure, the slits are synchronously moved to scan the object in a direction perpendicular to the slits such that both sets of slits and the x-ray source focal spot are maintained in the same plane. In this manner, the scattered radiation is prevented from reaching the x-ray conversion device. A drawback associated with this method is the difficulty in maintaining positional slit synchronism. Additionally, such apparatus is subject to reliability problems commonly encountered with moving parts of a mechanism.

SUMMARY OF THE INVENTION

Accordingly, it is an object of the invention to provide an improved x-ray imaging method in which the undesired effects of scatter are minimized.

It is another object of the invention to provide an improved method of x-ray imaging in which the effects of scatter are reduced electronically.

It is still another object of the invention to provide an improved method of x-ray imaging in which the effects of x-ray, electron, and optical scatter are minimized.

In accordance with the new method of imaging the internal features of an object, the object is scanned with a substantially planar beam x-ray radiation in a direction substantially orthogonal to the plane of the beam. The radiation is transmitted through the object in accordance with the respective attenuative properties of the internal features thereof and emerges as primary imaging radiation. The radiation emanating from the object, including the primary imaging radiation, is then converted to optical wavelength radiation suitable for detection by a television camera tube having a latent image integrating and storage element. In order to minimize the effects of scatter, predetermined regions of the storage element are erased immediately prior to exposing those regions to optical wavelength imaging radiation. The latent image created on the storage element by exposure thereof to the optical wavelength radiation having a reduced scatter contribution is read out so as to produce video signals suitable for driving, for example, a television monitor on which the latent image is displayed.

BRIEF DESCRIPTION OF THE DRAWING

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
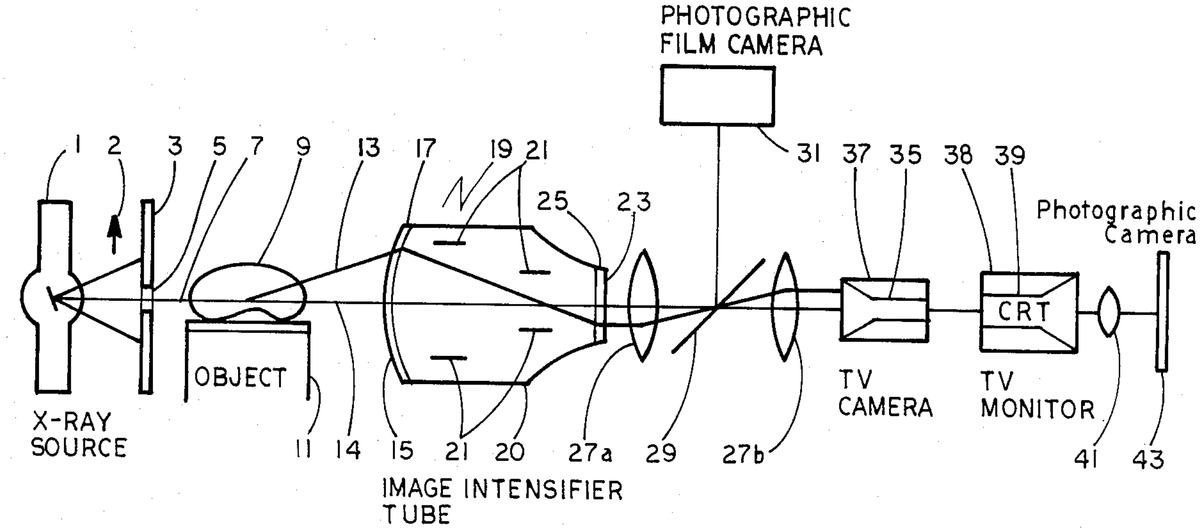
FIG. 1 depicts schematically an imaging apparatus useful with the method of the invention.

FIG. 1 illustrates schematically the imaging apparatus useful with the method of the invention. The apparatus includes an x-ray source 1, a table 11 for supporting patient 9, an image-intensifier tube 19, a conjugate lens pair 27a and 27b, a television camera 37, and a cathode-ray tube (CRT) 39 of a television monitor 38 for displaying a television image. A photographic camera 31 is also frequently included to photograph directly images produced on an output screen 25 of the image-intensifier tube. To this end, a dichroic mirror 29 is provided between lenses 27a and 27b. Mirror 29 is angled to divert a portion of optical wavelength radiation toward photographic camera 31, while allowing the remainder of the optical wavelength radiation to reach TV camera 37. The imaging apparatus may further include a photographic camera 43 for photographing an image on the CRT with the air of a lens 41. The apparatus additionally includes a slide 3 composed of a radiation-opaque material, such as lead, having an elongated opening (slit) 5 formed therein. Slide 3 is positioned between x-ray radiation source 1 and patient 9 and is adapted for movement is a direction substantially orthogonal to the long dimension of opening 5, as indicated by an arrow 2. In this manner, a substantially planar beam 7 of radiation admitted through opening 5 scans patient 9. The width of opening 5 may be selected to produce a primary radiation beam having a width of about ⅛ of an inch at face plate 15 of the image-intensifier tube. Typically, the opening is selected to provide a beam having a width of between 1/50 and 1/100 of the size of the object undergoing examination.

A television camera tube 35 (such as a vidicon) is provided in television camera 37 to scan images produced on output screen 25 of the image-intensifier tube. The construction and operation of the camera tube will be described in greater detail hereinafter.

Image-intensifier tube 19 is comprised of an evacuated envelope 20 having a face plate 15 and an output window 23. Primary x-ray imaging radiation 14 having passed through patient 9 impinges an input screen 17 situated on the inner surface of face plate 15 where it is converted by a phosphor and photocathode element (not shown separately) into an electron latent image. A plurality of internally positioned electrodes, such as electrodes 21, focus and accelerate the electrons toward a fluoroscent output screen 25 (located within the image-intensifier tube adjacent to output window 23) so as to produce a minified and intensified image thereon. The electrodes excite the phosphor in the fluoroscent screen to emit optical wavelength photons in proportion to impinging electron energy and density. In this manner, radiation selectively attenuated in accordance with the internal anatomical features of patient 9 is displayed as an optically detachable image at output screen 25.

Ideally, radiation beam 7 scanning patient 9 is selectively attenuated and emerges as primary imaging beam 14, for example, substantially unscattered. In practice, however, primary x-ray beam 7 is attenuated to a large extent by scatter in the patient so that scatter radiation, such as that designated 13, is also produced. Scatter radiation impinging input screen 17 causes spurious responses to also occur on output screen 25. Additionally, electrons produced in response to the primary and scatter radiation entering the image-intensifier tube may also undergo additional scatter in the image-intensifier tube causing further spurious responses to occur. Such spurious responses degrade image quality, as indicated hereinbefore.

Figure 2:
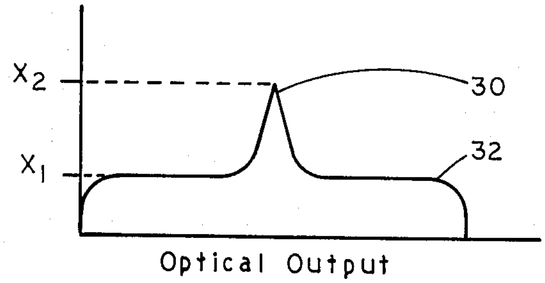
FIG. 2 depicts graphically the luminescent output of an x-ray image-intensifier tube resulting from a slit-determined exposure of the object, including responses due to both primary imaging and scattered radiation.

The manner in which image quality is degraded by scatter will be best understood if reference is made to FIG. 2 which depicts diagrammatically an exemplary intensity profile of the optical wavelength radiation at the image intensifier output screen 25 (FIG. 1). The luminescent output of screen 25 due to the primary imaging radiation 14 is designated 30, while the luminescent output due to scatter, such as x-ray scatter designated 13 (FIG. 1), and that due to electron scatter within image-intensifier tube 19 is designated 32 and represents the overall background illumination of the output screen. Image contrast may be defined as $$\text{Contrast} = \frac{X_2 - X_1}{\frac{X_2 + X_1}{2}},$$

wherein $X_2$ is the level of the output due to the primary imaging radiation and $X_1$ is the output level due to scatter radiation and electron scatter, so that it will be readily appreciated that as $X_1$ increases, image contrast decreases. It should also be noted that the image sensed by camera tube 35 would also include any optical scatter introduced by lenses 27a, 27b and mirror 29, resulting in additional decrease in contrast.

Figure 3:
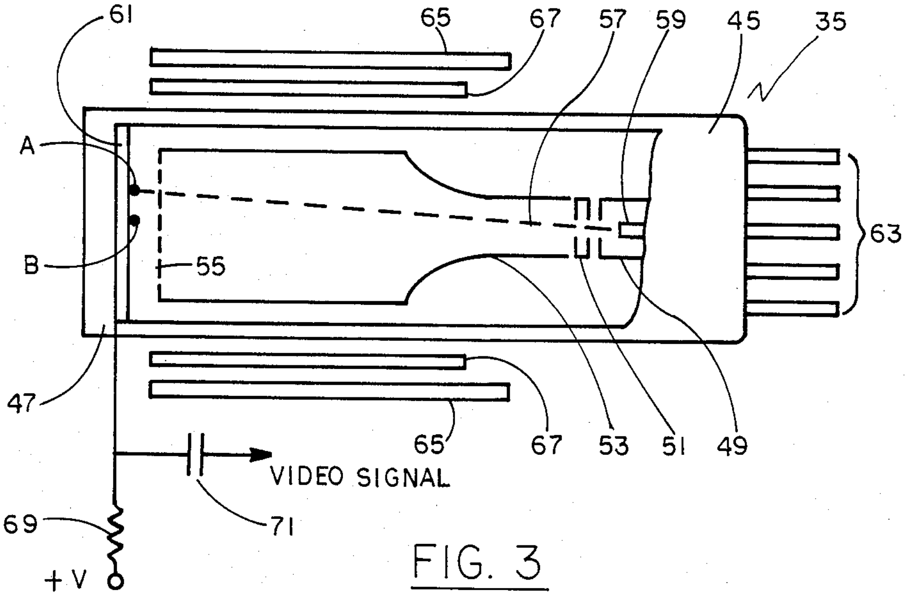
FIG. 3 is a schematic illustration of a vidicon television camera tube suitable for use with the method of the invention.

The conventional operation of a vidicon camera tube (commonly employed in many medical diagnostic applications) will be described next. A vidicon camera tube 35 is schematically depicted in FIG. 3. The tube includes an evacuated glass envelope 45 having a polished face plate 47. A number of control grids 49, 51, 53, and 55 are provided to control electrons emitted by a cathode 59. A plurality of pins 63 electrically connected to the various grid elements in a well-known manner are also provided at the base of the tube. An electrical coil 67 surrounds the camera tube and, along with the control grids, provides for the focussing of electrons emitted by the cathode into a beam 57 aimed toward a target 61. A series of electrical coils 65 also surround the camera tube and provide for the horizontal and vertical deflection of the electron beam so as to enable the beam to scan target 61. Target 61 is composed of two layers (not shown separately). A first layer is a transparent film of conductive materials applied directly to the inside surface of face plate 47 and forms the signal plate electrode. A second layer composed of a photo-conductive material (typically antimony trisulfide in a vidicon camera tube) is deposited over the transparent electrode.

In operation, the transparent electrode is coupled to a source voltage (V) of positive potential (relative to cathode 59) through a load resistor 69 so as to create a potential difference across the photo-conductive layer. The electrical resistance of the photo-conductive layer exhibits a dependence on the intensity of incident light (optical wavelength radiation). That is, the higher the intensity of the incident light, the lower the resistance of the material. It is beneficial to think of the photo-conductive layer as being made up of pixels (picture elements), each consisting of a parallel capacitor/resistor combination. Due to the electrical potentials applied to the transparent electrode and cathode, the capacitor in any given pixel is charged to cathode voltage by the scanning electron beam (raster scan). As the intensity of the incident light changes, the conductivity of the resistor changes, thereby discharging the capacitor by an amount proportional to the conductivity of the resistor. It will be apparent, therefore, that the collective positive electrical charge distribution on a target exposed to an optical wavelength image, such as that produced on the output screen of the image-intensifier tube, corresponds to the intensity of the light incident thereon. The target has an integrating and storing property due to target electrical capacitance in that, as the level of light incident thereon varies spatially, the level of charge distribution varies accordingly. The target maintains a given charge distribution, following exposure to optical wavelength radiation, thereby creating a latent image.

As known, information (video signals) corresponding to the charge distribution is read out in a line-by-line scan on the target with electron beam 57 by appropriately energizing horizontal and vertical deflection coil 65. As the electron beam scans across target 61, a current flows in load resistor 69 which is proportional to the spatially incremental stored charge. A video signal voltage is developed across the resistor and is coupled through a capacitor 71 to a video pre-amplifier (not shown) and used to drive a CRT in a television monitor. It should be noted that scanning the target for the purpose of reading out the latent image discharges the capacitors to cathode potential and results in the target being erased. The video signals obtained in this manner contain the desired imaging information exemplified by peak 30, as well as the unwanted scatter-induced information identified as 32 in FIG. 2.

In accordance with the method of the invention, effective scatter reduction by approximately one half may be realized by utilizing a controlled camera tube target erase. The controlled target erase consists of a camera tube target raster scanned by the electron beam that is controlled in the vertical position so as to immediately precede in position on the target the latent image charge pattern as integrated on the target by means of exposure by the x-ray single-slit scan process. That is, as slit 5 is moved in the direction of arrow 2 in FIG. 1, the primary optical output 30 (FIG. 2), due principally to the primary image radiation beam 14, moves in the same direction across output screen 25 of the image-intensifier tube and is optically imaged by lenses 27*a* and 27*b* on target 61 to form a latent image thereon. Electron beam 57 (FIG. 3) is caused to scan target 61 at a position A (FIG. 3) which immediately precedes target region B which is being exposed to the primary optical output 30. In this manner, the scatter-induced latent image that leads in position the desired latent image produced by optical radiation due primarily to the primary radiation (as controlled by the scanning slit) is erased from the target prior to exposing position A to primary optical output 30 and prior to read out. This reduces the effects due to x-ray scatter, electron scatter, and optical scatter in system light optics by an average factor of approximately one half of that which would otherwise be present. The one-half factor arises because scatter spatially following the erase scan is not erased. The x-ray grid and the dual-scanning slit methods, as previously described, have no affect on scatter originating in the image intensifier or the system light optics. Upon completion of the target erase in the manner described, the latent image may be conventionally read out with a second electron beam scan of the target. The video signal thusly obtained may be used to drive a television monitor for viewing or photographing. Alternatively, the signals may be conventionally recorded on video tape for analysis later.

A preferred application of the controlled target erase method described aboveis to obtain high quality television images on CRT 39 of the optical images appearing at the output of the image intensifier tube 19. The images displayed on CRT 39 may be then photographed to obtain high quality photographic images. To this end, the read-out electron beam scan of the target is performed at a slower rate than the normal rate of once every 1/60 second. The slower scan rate provides higher quality television images due to the less demanding bandwidth requirements and the resulting increase in the signal-to-noise ratio of the video signal output of the TV camera. Also, a TV image having improved spatial resolution is obtained since the slower scan is performed with a lower energy electron beam. By way of illustration, the latent image on target 61 is scanned with the read-out electron beam at a rate of between 1/60 second and 1/10 second. The sequence of scanning the object with the planar x-ray beam and the erase scan of the television camera target may be, for example, timed to occur once every second.

The target erase scan may be synchronized with the movement of slide 3 by slaving the vertical scan of camera tube 35 to the movement of the slide to just lead in position opening 5. This could be implemented, for example, by using a position-sensing device, such as a wiper potentiometer (not shown), to track the movement of slide 3. The normal horizontal camera tube scan would remain unchanged. It will be also appreciated by those of ordinary skill in the art that it may be necessary to reduce the bias on cathode 59 to avoid overcharging the target during the scatter-erase scan.

Although the preferred method of the invention has been described with reference to a vidicon tube, it should be noted that other camera tubes having a latent image storage element (such as image orthicons, isocons, lead-oxide vidicons, and various chalcognide vidicons) may also be employed with the method of the invention.

From the foregoing, it will be appreciated that the invention provides an improved method for minimizing the undesirable effects of scatter electronically. The resulting x-ray images have improved resolution, contrast, and noise properties.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

That which is claimed is:

1. A method of imaging the internal features of an object undergoing examination, comprising the steps of:

(a) scanning said object with a substantially planar beam of x-ray radiation in a direction substantially orthogonal to the plane of said beam, such that a fraction of said radiation is transmitted through said object in accordance with the attenuative properties of the internal features thereof as primary imaging radiation;

(b) converting radiation emanating from said object, including said primary imaging radiation, to optical wavelength radiation suitable for detection by television camera means having a latent image storage element;

(c) erasing a predetermined region of said storage element immediately prior to exposing said region to said optical wavelength radiation, including that produced by said primary imaging radiation, wherein exposure of said storage element to said optical wavelength radiation in the course of a scan creates a complete latent image on said storage element of the internal features of said object scanned by said x-ray beam;

(d) reading out, upon completion of said step of scanning, said complete latent image so as to produce video signals suitable for displaying said latent image on television monitor means.

2. The method of claim 1 further comprising the step of photographing the image displayed on said television monitor means.

3. The method of claim 1 wherein said step of reading out comprises scanning said latent image storage element with an electron beam at a rate less than 1/60 second per scan.

4. The method of claim 1 wherein said step of converting comprises converting said radiation emanating from said object to optical wavelength radiation by means of an x-ray image-intensifier tube.

5. The method of claim 4 wherein said television camera means comprises a television camera tube and wherein said latent image storage element comprises the target element of said camera tube.

6. The method of claim 5 wherein said step of erasing comprises scanning the target with an electron beam produced in said camera tube.

7. The method of claim 6 wherein said step of reading out comprises scanning the target with an electron beam upon completion of said step of scanning.

8. The method of claim 7 wherein said television camera means comprises a vidicon camera tube.

9. The method of claim 1 wherein said step of erasing comprises scanning said latent image storage element with an electron beam produced in said television camera means.

10. The method of claim 9 wherein said step of reading out comprises scanning said latent image storage element with an electron beam produced in said television camera means.

11. The method of claim 10 wherein said television camera means comprises a television camera tube and wherein said latent image storage element comprises a target element of said camera tube.

12. The method of claim 11 wherein said step of converting comprises converting said radiation emanating from said object to optical wavelength radiation by means of an x-ray image-intensifier tube.

13. The method of claim 11 wherein said step of reading out comprises scanning the target with an electron beam completion of said step of scanning.

14. The method of claim 11 wherein said television camera means comprises a vidicon camera tube.

* * * * *

UNITED STATES PATENT AND TRADEMARK OFFICE
CERTIFICATE OF CORRECTION

PATENT NO. : 4,493,096

DATED : Jan. 8, 1985

INVENTOR(S) : Richard J. Rieke

It is certified that error appears in the above-identified patent and that said Letters Patent is hereby corrected as shown below:

Column 1, line 14, after "imaging" insert --apparatus--;
Column 5, line 67, change "signal" to --signals--;
Column 6, line 4, change "aboveis" to --above is--.

Signed and Sealed this

*Seventeenth* Day of *September 1985*

[SEAL]

*Attest:*

DONALD J. QUIGG

*Attesting Officer*

*Commissioner of Patents and Trademarks—Designate*